(12) United States Patent
Jacquot et al.

(10) Patent No.: US 9,133,153 B2
(45) Date of Patent: Sep. 15, 2015

(54) METHOD FOR MANUFACTURING COMPOUNDS INCLUDING NITRILE FUNCTIONS

(71) Applicant: RHODIA OPERATIONS, Paris (FR)

(72) Inventors: Roland Jacquot, Francheville (FR); Philippe Marion, Vernaison (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 14/364,382

(22) PCT Filed: Dec. 13, 2012

(86) PCT No.: PCT/EP2012/075377
§ 371 (c)(1),
(2) Date: Jun. 11, 2014

(87) PCT Pub. No.: WO2013/087765
PCT Pub. Date: Jun. 20, 2013

(65) Prior Publication Data
US 2014/0343304 A1    Nov. 20, 2014

(30) Foreign Application Priority Data

Dec. 16, 2011  (FR) .................... 11 61823

(51) Int. Cl.
*C07D 307/68* (2006.01)
*C07D 307/14* (2006.01)
*C07D 307/24* (2006.01)
*C07D 307/66* (2006.01)

(52) U.S. Cl.
CPC ............. *C07D 307/68* (2013.01); *C07D 307/14* (2013.01); *C07D 307/24* (2013.01); *C07D 307/66* (2013.01)

(58) Field of Classification Search
CPC ........................................ C07D 307/68
USPC ........................................ 549/474
See application file for complete search history.

(56) References Cited

U.S. PATENT DOCUMENTS

| 4,743,702 A | 5/1988 | Hoelderich et al. |
| 2005/0059836 A1 | 3/2005 | Terasaka et al. |
| 2005/0187266 A1 | 8/2005 | Su |
| 2011/0288324 A1 | 11/2011 | Jacquot et al. |

FOREIGN PATENT DOCUMENTS

WO  2010/063632 A1  6/2010

*Primary Examiner* — Taofiq A Solola

(57) ABSTRACT

The present invention relates to the manufacture of compounds of general formula I or III including nitrile functions. Specifically, the invention relates to the manufacture of compounds including nitrile functions from compounds which include carboxyl functions and which are advantageously of natural and renewable origin.

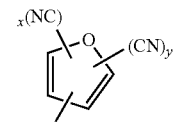

I

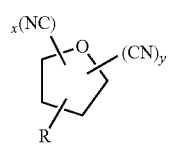

III

16 Claims, No Drawings

METHOD FOR MANUFACTURING COMPOUNDS INCLUDING NITRILE FUNCTIONS

This application is a U.S. national phase entry under 35 U.S.C. §371 of International Application No. PCT/EP2012/075377, filed on Dec. 13, 2012, which claims priority to French Application No. 1161823, filed on Dec. 16, 2011, the entirety of all of which are being incorporated herein by reference for all purposes.

The present invention relates to the manufacture of compounds comprising nitrile functional groups.

It relates more particularly to the manufacture of compounds comprising nitrile functional groups from compounds comprising carboxyl functional groups, advantageously of natural and renewable origin.

Compounds comprising nitrile functional groups are important for the manufacture of amine compounds. Dinitrile compounds result in amines which are, for example, monomers which are the source of polymers, such as polyamide, for example. Mononitrile compounds result in amines or in amides which are, for example, used for the manufacture of cationic surfactants.

Many processes for the synthesis of nitriles have been provided, in particular synthesis processes starting from ammonia and from carboxylic acids. These processes mainly use, as starting raw material, hydrocarbon compounds resulting from oil refining.

Given that oil resources are running out, many research studies are being undertaken in order to develop processes for the synthesis of these compounds, which are important in the manufacture of materials used in numerous applications, from raw materials or resources termed renewable, or from recycled raw materials, which are normally destroyed or given added value in the form of energy. These renewable resources can be obtained from cultivated or noncultivated vegetable matter, such as trees, plants, for example sugar cane, corn, cassava, wheat, rape, sunflower, palm, castor oil plant or the like.

This vegetable matter is converted by processes generally comprising several mechanical, chemical and biological stages.

2,5-Furandicarboxylic acid (FDCA) is in particular a product resulting from biomass (it can be obtained in particular from mucic acid or from hydroxymethylfurfural, which is obtained from cellulose). It is thus a priori a good candidate as starting material for preparing the corresponding biosource dinitrile.

The problem is that this compound (FDCA) is not very soluble in conventional solvents and in particular is not thermally stable: it decarboxylates to form furan, which is a carcinogenic, mutagenic or toxic for reproduction (CMR) chemical product.

Conventional processes for the preparation of nitrile by nitrilation of acids, which are processes at high temperature and under pressure, thus cannot be employed, in particular starting from FDCA.

The search is thus still under way for a process for the preparation of nitrile, from FDCA or derivatives, which does not exhibit these disadvantages.

To this end, the invention provides a process for the preparation of a compound of general formula (I):

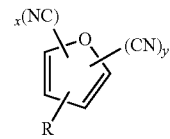

or of a compound of general formula (III):

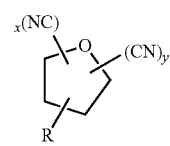

in which R symbolizes one or more optional substituents, x, y is equal to 0 or 1 with (x+y) equal to 1 or 2.

This process consists in reacting ammonia with a compound of general formula (II):

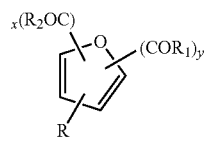

or with a compound of general formula (IV):

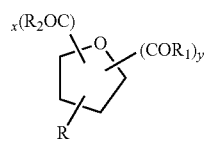

in which $R_1$ and $R_2$, which are identical or different, represent —$NH_2$ or —$ONH_4$ or —$OR_3$, $R_3$ being an alkyl group having from 1 to 4 carbon atoms,
and in which x, y and R have the meanings indicated above, in the presence of a catalyst comprising a crystalline silicon orthophosphate $Si_3(PO_4)_4$.

The compound of general formula (I) or (III) can carry one or more substituents.

Advantageously, the compound of general formula (II) or (IV) results from a renewable material of vegetable origin.

A renewable material or resource is a natural, animal or plant, resource, the stock of which can be reconstituted over a short period on the human time scale. It is in particular necessary for the stock to be able to be renewed as quickly as it is consumed.

Unlike materials resulting from fossil materials, renewable raw materials contain a high proportion of [14]C. Preferably, the nitriles of the invention consist of organic carbon resulting from renewable raw materials. Thus, this preferred characteristic might be certified by determining the $^{14}$C content according to one of the methods described in the standard ASTM D6866, in particular according to the mass spectrometry method or the liquid scintillation spectrometry method which are described in this standard.

These renewable resources are generally produced from cultivated or noncultivated vegetable matter, such as trees, plants, for example sugar cane, corn, cassava, wheat, rape, sunflower, palm, castor oil plant or the like.

For example, the compound of general formula (II) or (IV) can result from renewable resources, such as natural polysaccharides, such as starch or cellulose, it being possible for the starch to be extracted, for example, from wheat, corn or potato. It can in particular originate from various conversion processes, in particular conventional chemical processes, but also from enzymatic conversion processes or fermentation conversion processes.

For example, the compound of formula (II) can be obtained from 2,5-furandicarboxylic acid, which is itself obtained in particular from mucic acid or from hydroxymethylfurfural, which is obtained from cellulose.

Advantageously, R is chosen from:

linear or branched alkyl groups preferably having from 1 to 6 carbon atoms and more preferably still from 1 to 4 carbon atoms, linear or branched mono-, poly- or perhalogenated alkyl groups preferably having from 1 to 6 carbon atoms and from 1 to 13 halogen atoms and more preferably still from 1 to 4 carbon atoms and from 1 to 9 halogen atoms, ether $R_4$—O— or thioether $R_4$—S— groups in which $R_4$ represents a linear or branched alkyl group having from 1 to 6 carbon atoms and more preferably still from 1 to 4 carbon atoms or the phenyl group, acyloxy or aroyloxy $R_4$—CO—O— groups in which the $R_4$ group has the meanings given above, acyl or aroyl $R_4$—CO— groups in which the $R_4$ group has the meanings given above, the hydroxyl group, a halogen atom, preferably a fluorine atom.

Advantageously, $R_1$ and $R_2$ are —$OR_3$ groups. In other words, the compound of formula (II) or (IV) is an ester.

According to a specific embodiment of the process of the invention, x+y is equal to 2 and $R_1$ and $R_2$ are identical.

Preferably, the compound of formula (II) or (IV) is methyl 2,5-furandicarboxylate, ethyl 2,5-furan-dicarboxylate, ammonium 2,5-furandicarboxylate, methyl 2-furoate, ethyl 2-furoate or ammonium 2-furoate.

In accordance with the process of the invention, a gas stream comprising the compound of formula (II) or (IV) and ammonia is passed over the catalyst of the invention.

Although the amount of ammonia involved can be equal to the theoretical amount determined by the stoichiometry of the reaction (that is to say, 1 mol of ammonia per mole of ester functional group), it is preferably to carry out the reaction using an excess of ammonia. Generally, it is preferable to use at least 2 mol and more particularly from 2 to 10 mol of ammonia per mole of ester functional group. The excess of ammonia present in the gas stream resulting from the reaction can be recycled, after purification.

The apparent contact time of the gas stream with the catalyst, defined as the duration in seconds during which one unit of volume of gas mixture (measured under standard pressure and temperature conditions) is in contact with the unit of apparent volume of catalyst, can be between 0.001 s and 10 min and preferably between 0.01 s and 2 min.

The process is generally carried out at atmospheric pressure, at a temperature generally of between 200 and 600° C., preferably between 300° C. and 450° C. and more preferably still between 350° C. and 425° C.

The compound of formula (II) or (IV) is generally vaporized before it is brought into contact with the catalyst.

It can, for example, be vaporized in a vaporization device or by spraying into the superheated (300-400° C.) ammonia stream, generally after a preheating. These two methods of vaporization are given solely by way of indication.

The compound of formula (II) or (IV) is generally supplied, before it is vaporized, in the liquid form. It can be supplied in the molten form or in the solution form. It can be an aqueous solution or a solution in a solvent.

When $R_1$ and $R_2$ represent —$ONH_4$ in the formula (II) or (IV), the compound of formula (II) or (IV) is generally in the form of an aqueous solution. The maximum suitable concentration is set by the solubility limit of the compound of formula (II) or (IV) in water at the temperature for supplying the solution to the vaporization device used to supply the solution to the catalyst.

When $R_1$ and $R_2$ represent an —$OR_3$ group, that is to say when the compound of formula (II) or (IV) is an ester, this compound can be in the molten form or in the form of a solution in a solvent, advantageously an alcohol or an ether. Preferably, use is made of the alcohol which was employed during the preparation of the ester compound of formula (II) or (IV).

The maximum suitable concentration is set by the solubility limit of the compound of formula (II) or (IV) in the solvent at the temperature for supplying the solution to the vaporization device used to supply the solution to the catalyst.

Mention may be made, as an example of the solvent, for example, of methanol, ethanol, THF, 1,4-dioxane or dimethoxyethane.

Advantageously, the catalyst comprises less than 5% by weight of amorphous silicon orthophosphate.

A catalyst suitable for the invention can advantageously be obtained by impregnating a silica with phosphoric acid in aqueous solution, followed by calcination under air, in order to form the silicon orthophosphate. The calcination temperature is advantageously between 450° C. and 800° C., for example between 450° C. and 550° C. Such a manufacturing process is described in particular in the French patent application No. 2 810 317.

It is also possible to use catalysts sold by various companies, such as UOP. However, it may be necessary to treat these commercial catalysts in order to increase the content of crystalline form, for example by heat treatment.

The catalyst is generally in the solid form, for example in the form of beads, cylindrical extrudates, honeycomb or the like. The catalyst is generally positioned in a reactor in the form of a fixed bed through which the compound of formula (II) or (IV) and the ammonia in the vapor form are sent.

The catalyst of the invention can also comprise doping elements or cocatalysts.

According to another characteristic of the invention, the catalyst used for the implementation of the process of the invention can be regenerated by treatment of the catalyst bed with air at a temperature of between 450 and 500° C. for 10 to 20 hours. The regeneration treatment can be monitored by detection of the presence of $CO_2$ in the air at the reactor outlet. The treatment is halted when the absence of $CO_2$ in the air is observed. The catalyst thus regenerated can be used for a fresh implementation of the process of the invention with an equivalent catalytic performance.

The vapors recovered at the reactor outlet are condensed in order to recover the compound comprising the nitrile functional groups. These compounds can subsequently be purified by conventional techniques, such as distillation, crystallization, extraction or the like.

The catalyst is advantageously activated, in particular by treatment with air at a temperature of between 350° C. and 500° C., before supplying the compound (II) or (IV).

According to a specific embodiment of the invention, the nitrile of formula (I) or (III) thus recovered is hydrogenated in order to form the corresponding amine, according to a method known to a person skilled in the art. Thus, an amine is obtained, all the carbons of which are biosourced (as resulting from a biosourced carboxylic acid, that is to say a carboxylic acid resulting from a renewable starting material). The diamines can be used as starting materials in the manufacture of polyamides, which will thus be partially or completely biosourced depending on the acids used for the polymerization. The amines can also be used to prepare surfactants.

According to another specific embodiment of the invention, the nitrile of formula (I) thus recovered is hydrogenated in order to form the amine of formula (V):

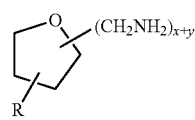

Other details or advantages of the invention will become more clearly apparent in the light of the examples given below.

EXAMPLES

Example 1

Use is made of a tubular stainless steel reactor having an internal diameter of 2.54 cm which is equipped with a 1 mm temperature probe and which is heated by an electric tube furnace. The catalytic bed, composed of 3 ml of catalyst originating from UOP, referenced SPA1, ground and sieved between 2 and 3 mm, is activated under a stream of air of 3 l/h at 450° C. over 15 hours.

After this activation, the catalytic bed is brought back to 400° C. and the stream of air is replaced with a stream of ammonia of 2.7 l/h. The catalytic bed is then reheated to 425° C. and a 20% w/w methanolic methyl 2,5-furandicarboxylate solution is injected onto the catalytic bed at a flow rate of 6 ml/h while maintaining the ammonia flow rate at 2.7 l/h. After injecting 50 ml, the condensate is analyzed by a GC. A yield of 12% of 2,5-dicyanofuran is then obtained for a conversion of the diester of 38%.

Example 2

Use is made of a tubular stainless steel reactor having an internal diameter of 2.54 cm which is equipped with a 1 mm temperature probe and which is heated by an electric tube furnace. The catalytic bed, composed of 3 ml of catalyst originating from UOP, referenced SPA1, ground and sieved between 2 and 3 mm, is activated under a stream of air of 3 l/h at 450° C. for 15 hours. After this activation, the catalytic bed is brought back to 400° C. and the stream of air is replaced with a stream of ammonia of 2.7 l/h. The catalytic bed is then reheated to 425° C. and a 20% by weight ethanolic ethyl 2,5-furandicarboxylate solution is injected onto the catalyst at a flow rate of 5 ml/h while maintaining the ammonia flow rate at 2.7 l/h.

After 50 ml of injected solution, the condensate is analyzed by GC. A dinitrile yield of 15% is obtained for a conversion of the diester of 30%.

Example 3

Use is made of a tubular stainless steel reactor having an internal diameter of 2.54 cm which is equipped with a 1 mm temperature probe and which is heated by an electric tube furnace. The catalytic bed, composed of 3 ml of catalyst originating from UOP, referenced SPA1, ground and sieved between 2 and 3 mm, is activated under a stream of air of 3 l/h at 450° C. for 15 hours. After this activation, the catalytic bed is brought back to 400° C. and the stream of air is replaced with a stream of ammonia of 2.4 l/h. The catalytic bed is then reheated to 425° C. and a solution of ethyl 2,5-furandicarboxylate in THF at a w/w concentration of 45% is then injected onto the catalyst at a flow rate of 1.5 ml/h while maintaining the ammonia flow rate of 2.4 l/h. After injecting 50 ml, the condensate is analyzed by GC. A dinitrile yield of 14% and an ester nitrile yield of 28% are obtained for a conversion of the diester at 45%.

Example 4

Regeneration of the Catalyst

The catalyst can, when its activity decreases, be regenerated by a heat treatment in the presence of air. A stream of air is passed at a flow rate of 10 l/h over the cold catalytic bed and heating to 500° C. is carried out gradually over 4 hours. These conditions are subsequently maintained for 15 hours. The gases exiting from the reactor have to be devoid of $CO_2$.

The temperature is subsequently brought back to 400° C. under 10 l/h of nitrogen and, at this temperature, the flow rate of nitrogen is gradually replaced with a flow rate of ammonia. An exotherm should not be observed. The catalyst is then regenerated.

The invention claimed is:
1. A process for the preparation of a compound of general formula (I):

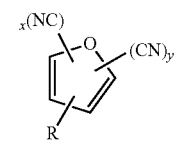

or respectively of a compound of general formula (III):

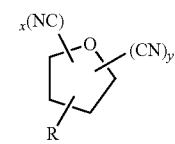

in which R symbolizes one or more optional substituents, x and y are each equal to 0 or 1 with (x+y) equal to 1 or 2, the process consisting of reacting, in the vapor phase, ammonia with a compound of general formula (II):

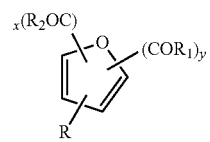

or respectively with a compound of general formula (IV):

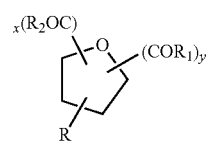

in which $R_1$ and $R_2$, which are identical or different, represent —$OR_3$, $R_3$ being an alkyl group having from 1 to 4 carbon atoms, and wherein R is chosen from:
- linear or branched alkyl groups,
- linear or branched mono-, poly- or perhalogenated alkyl groups,
- ether $R_4$—O— or thioether $R_4$—S— groups in which $R_4$ represents a linear or branched alkyl group having from 1 to 6 carbon atoms or the phenyl group,
- acyloxy or aroyloxy $R_4$—CO—O— groups in which the $R_4$ group has the meanings given above,
- acyl or aroyl $R_4$—CO— groups in which the $R_4$ group has the meanings given above,
- the hydroxyl group,
- a halogen atom;

in the presence of a catalyst comprising a silicon orthophosphate of formula $Si_3(PO_4)_4$.

2. The process as claimed in claim 1, wherein the compound of formula (II) and/or of formula (IV) results from a renewable material of vegetable origin.

3. The process as claimed in claim 1, wherein x+y is equal to 2 and $R_1$ and $R_2$ are identical.

4. The process as claimed in claim 1, wherein the compound of formula (II) or of formula (IV) is selected from the group consisting of methyl 2,5-furandicarboxylate, ethyl 2,5-furandicarboxylate, methyl 2-furoate, and ethyl 2-furoate.

5. The process as claimed in claim 1, wherein the reaction is carried out at a temperature of between 300 and 450° C.

6. The process as claimed in claim 1, wherein the reaction is carried out in a reactor comprising a fixed catalytic bed.

7. The process as claimed in claim 1, wherein the catalyst is obtained by impregnating a silica with phosphoric acid and calcination under air.

8. The process as claimed in claim 7, wherein the calcination is carried out at a temperature of between 400° C. and 800° C.

9. The process as claimed in claim 1, wherein at least the nitrile (I) and/or (III) formed is hydrogenated in order to form the corresponding amine.

10. The process as claimed in claim 1, wherein at least the nitrile (I) formed is hydrogenated in order to form the amine of general formula (V):

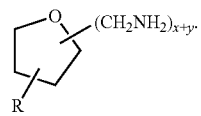

11. The process according to claim 1, wherein linear or branched alkyl groups have from 1 to 6 carbon atoms.

12. The process according to claim 1, wherein linear or branched alkyl groups have from 1 to 4 carbon atoms.

13. The process according to claim 1, wherein linear or branched mono-, poly- or perhalogenated alkyl groups have from 1 to 6 carbon atoms and from 1 to 13 halogen atoms.

14. The process according to claim 1, wherein linear or branched mono-, poly- or perhalogenated alkyl groups have from 1 to 4 carbon atoms and from 1 to 9 halogen atoms.

15. The process according to claim 1, wherein $R_4$ represents a linear or branched alkyl group having from 1 to 4 carbon atoms.

16. The process according to claim 1, wherein halogen atom is a fluorine atom.

* * * * *